United States Patent
De Corral et al.

(10) Patent No.: US 10,335,753 B2
(45) Date of Patent: Jul. 2, 2019

(54) FLUID MIXER ASSEMBLY

(71) Applicant: Waters Technologies Corporation, Milford, MA (US)

(72) Inventors: Jose De Corral, Grafton, MA (US); Neal B. Almeida, Cumberland, RI (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 897 days.

(21) Appl. No.: 14/830,611

(22) Filed: Aug. 19, 2015

(65) Prior Publication Data
US 2016/0184786 A1 Jun. 30, 2016

Related U.S. Application Data

(63) Continuation of application No. 11/631,221, filed as application No. PCT/US2005/023392 on Jun. 29, 2005, now abandoned.
(Continued)

(51) Int. Cl.
B01F 3/08 (2006.01)
B01F 5/00 (2006.01)
(Continued)

(52) U.S. Cl.
CPC ........ B01F 15/0243 (2013.01); B01D 15/166 (2013.01); B01F 3/0861 (2013.01);
(Continued)

(58) Field of Classification Search
CPC .. B01F 15/0243; B01F 3/0681; B01F 5/0077; B01F 5/0268; B01F 5/0602;
(Continued)

(56) References Cited

U.S. PATENT DOCUMENTS 3,905,395 A    9/1975 Hupe
4,204,775 A *  5/1980 Speer .................. B01F 5/0647
                                                  366/336
(Continued)

FOREIGN PATENT DOCUMENTS

JP      2152532 A       6/1990
JP      03277966 A  * 12/1991
(Continued)

OTHER PUBLICATIONS

English-Language Translation of JP 03-277966 A.*
(Continued)

*Primary Examiner* — James C Goloboy

(57) ABSTRACT

Disclosed is an assembly for mixing fluids (i.e., gases or liquids), and more particularly an assembly that accurately mixes two or more high-pressure fluid sources and is adapted for use in applications, such as for example, chromatography. The mixer assembly (100) includes, inter alia, a housing (10), an inlet fitting (40), and a mixer cartridge assembly (60). The housing (10) has a fluid receiving section (16) and a fluid discharge section (18) with an outlet (20) formed therein. A central bore (22) extends between the fluid receiving section (16) and fluid discharge section (18). An inlet fitting (40) is engaged with the housing (10) and has first (42) and second (44) fluid ports formed therein that extend from the fitting exterior to the fluid receiving section (16) of the housing (10). A mixer cartridge assembly (60) is disposed within the central bore (22) of the housing (10) and is positioned between the inlet fitting (40) and the downstream end portion of the housing (10). The mixer cartridge assembly (60) includes a body portion (64), a plurality of spheres disposed within a central mixing chamber (62) formed in the body portion (64), and mechanism for retaining the spheres in the mixing chamber (62).

18 Claims, 3 Drawing Sheets

Related U.S. Application Data

(60) Provisional application No. 60/587,581, filed on Jul. 13, 2004.

(51) Int. Cl.
| | | |
|---|---|---|
| *B01F 5/02* | (2006.01) | |
| *B01F 5/06* | (2006.01) | |
| *B01D 15/16* | (2006.01) | |
| *B01F 15/02* | (2006.01) | |
| *G01N 30/06* | (2006.01) | |
| *G01N 30/34* | (2006.01) | |

(52) U.S. Cl.
CPC .......... *B01F 5/0077* (2013.01); *B01F 5/0268* (2013.01); *B01F 5/0602* (2013.01); *B01F 5/0695* (2013.01); *B01F 5/0696* (2013.01); *G01N 30/06* (2013.01); *G01N 30/34* (2013.01); *G01N 2030/347* (2013.01)

(58) Field of Classification Search
CPC .... B01F 5/0695; B01F 5/0696; B01D 15/166; G01N 30/06; G01N 30/34; G01N 2030/347
See application file for complete search history.

(56) References Cited

U.S. PATENT DOCUMENTS

| | | |
|---|---|---|
| 4,270,921 A | 6/1981 | Graas |
| 6,790,361 B2 | 9/2004 | Wheat et al. |
| 7,287,898 B2 * | 10/2007 | Pauser ................ B01F 7/00008 222/145.5 |
| 7,875,361 B2 | 1/2011 | Hala et al. |
| 2002/0153433 A1 * | 10/2002 | Hunter ................ B05B 7/0408 239/290 |
| 2004/0042340 A1 | 3/2004 | Aso |
| 2010/0176043 A1 | 7/2010 | Wheat et al. |

FOREIGN PATENT DOCUMENTS

| | | | |
|---|---|---|---|
| JP | 03277966 A | 12/1991 | |
| JP | 2004516474 T | 6/2004 | |
| WO | WO-02/050531 | 6/2002 | |
| WO | WO-02074426 A1 * | 9/2002 | .......... B01F 7/00008 |

OTHER PUBLICATIONS

Japanese Patent Application No. 2007-521492 Office Action dated Dec. 7, 2010.

Japanese Patent Application No. 2007-521492 Office Action dated Feb. 7, 2012.

* cited by examiner

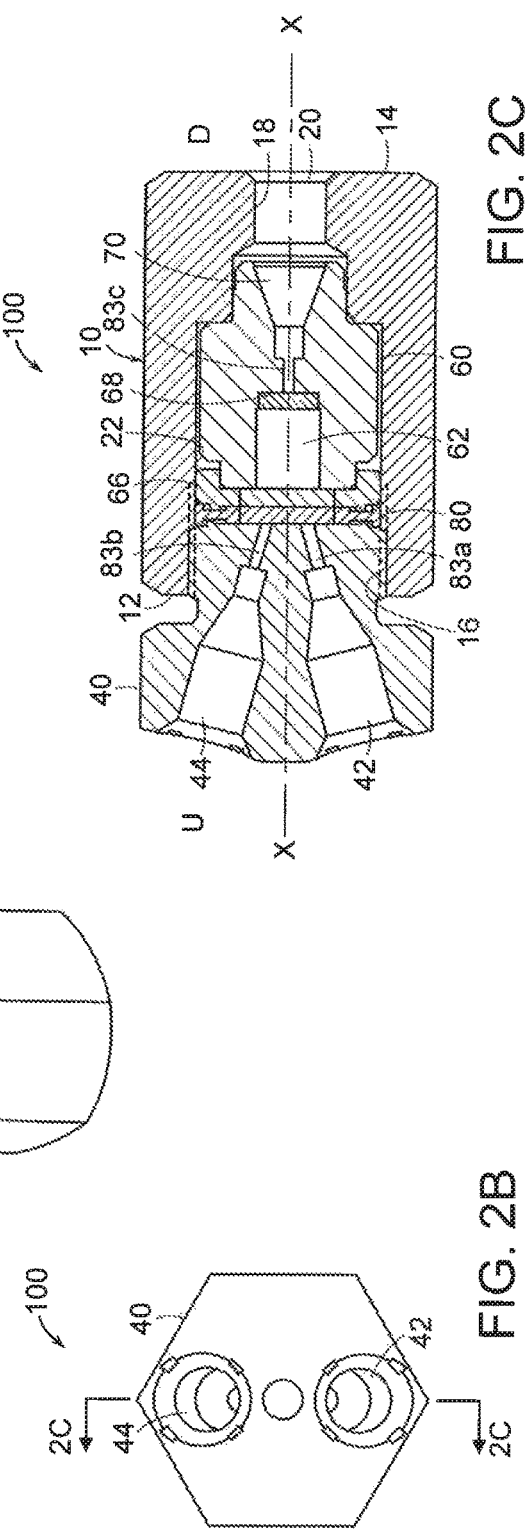

FLUID MIXER ASSEMBLY

RELATED APPLICATION

This application is a Continuation of U.S. patent application Ser. No. 11/631,221, filed May 6, 2009, which application is a U.S. national phase application, pursuant to 35 U.S.C. § 371, of PCT international application Ser. No. PCT/US2005/023392, filed Jun. 29, 2005, designating the United States and published in English on Feb. 16, 2006 as publication WO 2006/017039A1, which claims priority to U.S. provisional application Ser. No. 60/587,581, filed Jul. 13, 2004. The entire contents of the aforementioned patent applications are incorporated herein by this reference.

BACKGROUND OF THE INVENTION

1. Field of the Invention

The subject invention relates to an assembly for mixing fluids (i.e., gases or liquids), and more particularly to an assembly that accurately mixes two or more high-pressure fluid sources and is adapted for use in applications, such as for example, chromatography.

2. Background of the Related Art

In many chemical or industrial processes and applications, the need to accurately mix or combine two or more fluids is a necessary and important step in the production line. For example, in a chromatographic process, the accuracy of the solvent mixture (i.e., mixture of two or more solvents) affects the precision and accuracy of the subsequent chromatographic analysis.

Chromatography is a process for separating mixtures by virtue of their differences in absorbency. FIG. 1 illustrates a typical chromatographic process. Although there are other types of chromatography (e.g. paper and thin layer), most modern applications include a mobile phase and a stationary phase and the separation of the fluid mixture takes place in a column. The column is usually a glass or metal tube of sufficient strength to withstand the pressures that may be applied across it. The column can be for example, a packed bed or open tubular column. The column contains the stationary phase of the process, i.e., the material for which the components to be separated have varying affinities. The mobile phase of the chromatographic process is comprised of a solvent mixture into which the sample to be analyzed is injected. The mobile phase enters the column and the sample is absorbed onto the stationary phase. The solvent mixture is not absorbed on the stationary phase, but passes through the column.

The materials that comprise the mobile and the stationary phase vary depending on the general type of chromatographic process being performed, i.e., gas or liquid chromatography. The mobile phase in gas chromatography is generally an inert gas. The stationary phase is generally an adsorbent or liquid distributed or the surface of a porous, inert support. The mobile phase in liquid chromatography is a liquid of low viscosity that flows through the stationary bed. This may be comprised of an immiscible liquid coated onto a porous support, a thin film of liquid phase bonded to the surface of a sorbent, or a sorbent of controlled pore size.

As illustrated in FIG. 1, a first pump is used to draw a first solvent from a tank and supply it at a desired flow velocity and pressure to a T-shaped piping connector. A second pump is used to draw a second solvent from a second tank and supply it at a desired flow velocity and pressure to the T-shaped piping connector. At the T-shaped piping connector, the solvents are blended to achieve a solvent mixture having desired properties. The flow velocity of each solvent can be adjusted over time so as to vary the composition of the solvent mixture over time. A variation in the solvent mixture over time is called a solvent or compositional gradient.

A third pump is used to supply the sample or feed to a second T-shaped piping connection where it is injected into the solvent mixture and blended therewith, forming the mobile phase. The mobile phase runs through the column typically by action of the first and second pumps whereby the sample is absorbed onto the stationary phase. As the sample flows through the column, its different components will adsorb to the stationary phase to varying degrees. Those with strong attraction to the support move more slowly than those with weak attraction and this is how the components are separated. After the sample is flushed or displaced from the stationary phase, the different components will elute from the column at different times. The components with the least affinity for the stationary phase will elute first, while those with the greatest affinity for the stationary phase will elute last. A detector analyses the emerging stream by measuring a property, which is related to concentration and characteristic of chemical composition. For example, the refractive index or ultra-violet absorbance is measured.

In high pressure, low dead volume chromatography applications, uniform solvent mixtures and precise solvent gradients are required and consequently, very precise flow streams from the solvent pumps are necessary. A solvent flow transient caused by either the first or the second pump produces a solvent gradient error that affects the precision and accuracy of the chromatographic analysis. Unfortunately, all presently available pumps have flow transients to some extent.

In view of the above, there is a need for a mixer assembly that is capable of mixing two or more fluid streams without adding significant dead volume to the system and produces a uniform combined stream that relaxes the need for very precise flow delivery from the system pumps.

SUMMARY OF THE INVENTION

The invention provides a device or mixer assembly that accurately mixes two or more streams of fluids, even at high pressure. The mixer assembly includes a housing that has opposed upstream and downstream end portions. The upstream end portion of the housing has a fluid receiving section and the downstream end portion includes a fluid discharge section with a fluid outlet formed therein. The housing of the mixer assembly defines a central bore which extends between the fluid receiving section and fluid discharge section.

An inlet fitting is engaged with the upstream end portion of the housing and has first and second fluid inlet ports formed therein that extend from the fitting exterior to the fluid receiving section of the housing.

A mixer cartridge assembly is disposed within the central bore of the housing and is positioned between the inlet fitting and the downstream end portion of the housing. The mixer cartridge assembly includes a body portion, a plurality of spheres disposed within a central mixing chamber formed in the body portion, and mechanism for retaining the spheres in the mixing chamber.

The central mixing chamber formed in the body portion of the mixer cartridge communicates with the fluid receiving section of the housing and the discharge port extends from the mixing chamber to the fluid outlet formed in the housing.

The plurality of spheres disposed within the mixing chamber facilitates the mixing of fluids received therein.

In one preferred embodiment, the mechanism for retaining the spheres within the mixing chamber includes a filter ring associated with the upstream end of the mixing chamber and a filter disc associated with a downstream end of the mixing chamber.

It is envisioned that the mixer assembly can further include a filter element that is axially disposed between the inlet fitting and the mixer cartridge assembly. The filter element removes unwanted particles from the fluid provided from each of the first and second inlet ports to the mixing chamber.

In a preferred embodiment, the inlet fitting includes a male thread series that corresponds to a female thread series formed on the upstream end portion of the housing. It is also envisioned that the fluid inlet ports extend at an oblique angle with respect to the mixer assembly axis and the fluid provided by the first inlet port first contacts fluid provided by the second inlet port in the mixing chamber.

The present invention also provides a chromatographic system that includes, inter alia, first and second solvent tanks, first and second pumps for drawing solvents from the tanks, and a mixer assembly. The first pump conditions a first solvent to have a desired pressure and flow velocity and the second pump conditions the second solvent to have a desired pressure and flow velocity.

The mixer assembly includes a housing that has opposed upstream and downstream end portions. The upstream end portion of the housing has a fluid receiving section and the downstream end portion includes a fluid discharge section with a fluid outlet formed therein. The housing of the mixer assembly defines a central bore which extends between the fluid receiving section and fluid discharge section.

An inlet fitting is engaged with the upstream end portion of the housing and has first and second fluid inlet ports formed therein that extend from the fitting exterior to the fluid receiving section of the housing.

A mixer cartridge assembly is disposed within the central bore of the housing and is positioned between the inlet fitting and the downstream end portion of the housing. The mixer cartridge assembly includes a body portion, a plurality of spheres disposed within a central mixing chamber formed in the body portion, and mechanism for retaining the spheres in the mixing chamber.

The central mixing chamber formed in the body portion of the mixer cartridge communicates with the fluid receiving section of the housing and the discharge port extends from the mixing chamber to the fluid outlet formed in the housing. The plurality of spheres disposed within the mixing chamber facilitates the mixing of fluids received therein.

The disclosed mixer assembly is capable of mixing two or more fluid streams without adding significant dead volume to the system and produces a uniform combined stream that relaxes the need for very precise flow delivery from the system pumps.

BRIEF DESCRIPTION OF THE DRAWINGS

So that those having ordinary skill in the art to which the disclosed system appertains will more readily understand how to make and use the same, reference may be had to the drawings wherein:

FIG. 2A is a perspective view of a fluid mixer assembly of the present invention;

FIG. 2B is a top elevational view of the fluid mixer assembly of FIG. 2A;

FIG. 2C is a cross-sectional view of the fluid mixer assembly of FIGS. 2A and 2B taken along line A-A of FIG. 2B;

Figure 1:
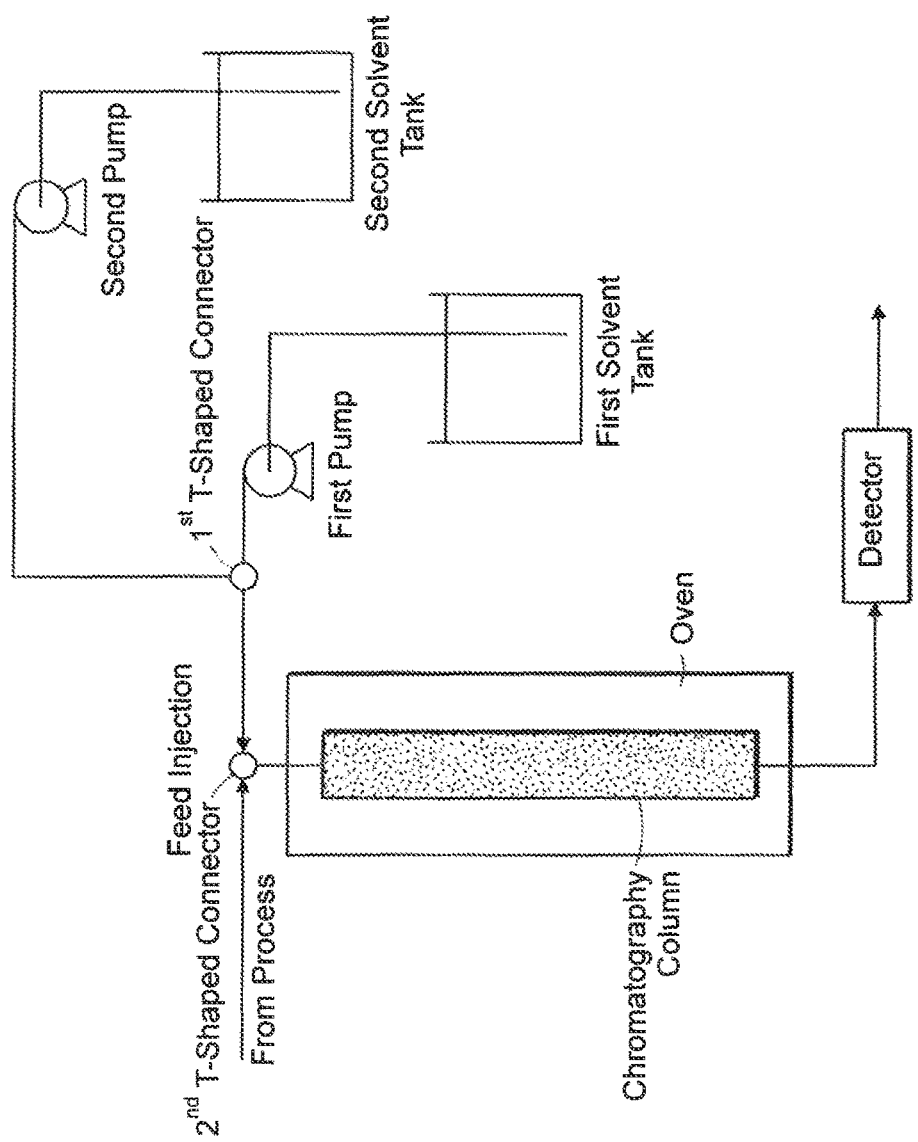
FIG. 1 is a schematic overview of a typical chromatographic system in which an embodiment of the present invention may be used.

These and other features of the mixer assembly of the present application will become more readily apparent to those having ordinary skill in the art from the following detailed description of the preferred embodiments.

DETAILED DESCRIPTION OF PREFERRED EMBODIMENTS

Fluid mixer assemblies in accordance with the invention are useful in a variety of applications that require two or more fluid streams to be mixed without adding significant volume to the system. Certain specific embodiments of the invention are described in detail below.

Referring now to the drawings, there is illustrated in FIGS. 2A through 2C, a mixer assembly constructed in accordance with a preferred embodiment of the subject invention and designated generally by reference numeral 100. In FIG. 2C, "U" designates the upstream end of the mixer assembly 100 and "D" designates the downstream end. Mixer assembly 100 represents one embodiment of the invention that can be used in a variety of applications that require two fluid streams to be mixed without adding significant volume to the system.

Mixer assembly 100 includes, inter alia, a housing 10, an inlet fitting 40 and a mixer cartridge 60. The housing 10 has opposed upstream and downstream end portions, 12 and 14, respectively. The upstream end portion 12 of the housing 10 has a fluid receiving section 16 and the downstream end portion 14 includes a fluid discharge section 18 having a fluid outlet 20 formed therein. The housing 10 of the mixer assembly 100 defines a central bore 22 which extends axially between the fluid receiving section 16 and fluid discharge section 18. The central bore 22 has a generally cylindrical outer circumference which is adapted for receiving the mixer cartridge 60.

An inlet fitting 40 is engaged with the upstream end portion 12 of the housing 10 and has a first fluid inlet port 42 and second fluid inlet port 44 formed therein. The inlet ports 42 and 44 extend from the fitting exterior to the fluid receiving section 16 of the housing 10. As shown in FIG. 2C, the inlet ports 42 and 44 are formed at an angle with respect to the central axis "X" of the mixer assembly 100. Additionally, the downstream ends of the inlet ports 42 and 44 do not intersect within the inlet fitting 40, but are angled so that the fluid streams exiting therefrom disperse in first and second frits/filter discs and then collide within mixing chamber 62 of cartridge 60.

Both the housing 10 and the inlet fitting 40 have a hexagonal exterior surface which facilitates the engagement of corresponding male and female threads, which are associated with the fitting and the upstream end portion of the housing, respectively. Those skilled in the art will recognize that other means can be used for securing the inlet fitting to the housing, such as for example, interlocking cam lugs.

Figure 3A:
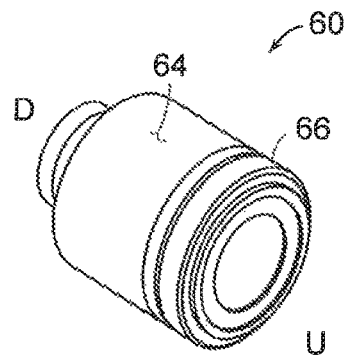
FIG. 3A is a perspective view of a fluid mixer cartridge of the present invention.
Figure 3B:
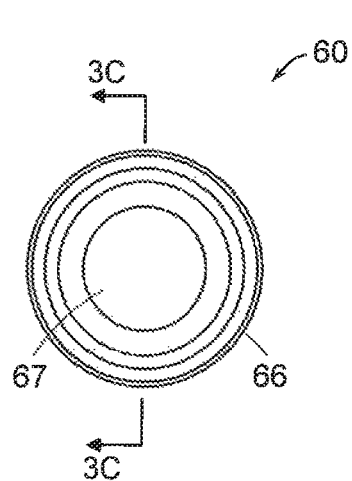
FIG. 3B is a top elevational view of the fluid mixer cartridge of FIG. 3A.
Figure 3C:
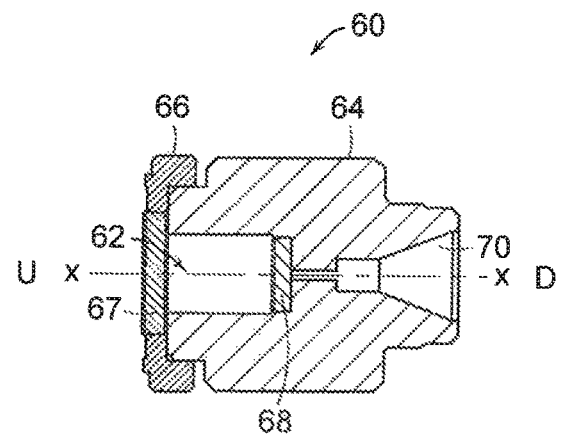
FIG. 3C is a cross-sectional view of the fluid mixer cartridge of FIGS. 3A and 3B taken along line A-A of FIG. 3B.

Mixer cartridge assembly 60 is disposed within the central bore 22 of the housing and is positioned between the inlet fitting 40 and the downstream end portion 18 of the housing 10. The mixer cartridge assembly 60 is illustrated in FIGS. 3A through 3C and includes a body portion 64 and a plurality of spheres (not shown) disposed within a central mixing chamber 62 formed in the body portion. The spheres are retained within the mixing chamber 62 by a filter disc 67 included in ring 66 associated with the upstream end of the mixing chamber 60 and a filter disc 68 associated with a downstream end of the mixing chamber 62. Preferably the spheres are made of glass, but those skilled in the art will readily appreciate that the spheres can be fabricated from other materials as dictated by the application for the mixer assembly (e.g., metal, plastic etc.). The gage of the filter disc 67 and 68 is selected so that the spheres are retained within the mixing chamber 62, but the fluid enters and exits the mixing chamber relatively unobstructed. The filter ring 66 holds the filter disc 67 in place. In alternative embodiments, other mechanisms can be employed for retaining the spheres within the mixing chamber without departing from the inventive aspects of the present disclosure. For example, the spheres can be placed within a net or porous enclosure. Alternatively, the sphere can have a diameter that is larger than the diameters of fluid passages 83a-83c (shown in FIG. 2c).

The central mixing chamber 62 formed in the body portion of the mixer cartridge 60 communicates with the fluid receiving section 16 of the housing 10 and a discharge port 70 extends from the mixing chamber 62 to the fluid outlet 20 formed in the housing 10. The plurality of spheres disposed within the mixing chamber facilitates the mixing of fluids received therein.

Mixer assembly 100 also includes a prefilter ring 80 that is positioned within the central bore 22 and adjacent to the inlet fitting 40. Prefilter ring 80 prevents particulate, which may be contained in the supplied fluid from entering the mixing chamber.

In operation, a first fluid stream, such as a solvent, is supplied to the first inlet port 42 by a first pump and a second fluid stream, such as a second solvent, is supplied to the second inlet port 44 by a second pump. Each fluid exits the inlet fitting 40 at prefilter ring 80 and is filtered and dispersed prior to entering the mixing chamber through the filter disc 67. The spheres contained within the mixing chamber 62 cause the two fluid streams to collide and mix in a uniform manner. The uniformly mixed fluid then exits the mixing chamber through the filter disc 68 and discharge port 70 and proceeds to the fluid outlet 20 of the mixer assembly 100.

The size of the mixing chamber 62 is selected so as to be of sufficient size to offset the flow velocity errors associated with solvent pumps. For example, if the first and second solvent pumps exhibit flow velocity errors that average out over a period of time "t", then the size of the mixing chamber is selected such that the time necessary for the blend to pass through the mixer is greater than time "t." Over the period of time "t", each pump draws a volume of fluid from the tank. The free volume within the mixing chamber is a function of the overall size of the mixing chamber. The mixer performance is a function of the number and size of the spheres. Therefore, all of the above-described parameters are selectively adjusted so that the time necessary for the blend to pass through the mixer is greater than time "t."

It should be noted that it is desirable to keep the size of the mixing chamber as small as practicable, thereby limiting the dead volume in the system (e.g., the volume of the fluid system from the entrance of the mixing chamber to the column). Dead volume in a chromatographic system is undesirable. During the chromatographic process, changes in the solvent composition are commanded. It is desired that these commands result in a stepped change in the solvent mixture. However, if there is too much dead volume in the system, the stepped change in the mixture is smoothed out, thereby adversely impacting the accuracy of the chromatographic analysis.

Mixer assembly 100 produces a uniform combined fluid mix that relaxes the need for very precise flow delivery from the solvent supply pumps. Still further, mixer assembly 100 combines in a single device what, traditionally, would have been three devices: a tee, a filter, and a mixer.

Those skilled in the art would readily appreciate that the disclosed mixer assembly can be used in any number of different fluid applications and is not limited to chromatographic applications. Moreover, a variety of materials can be used to form the parts of the mixer assembly, such as for example, stainless steel or plastic.

Although the invention has been described with respect to preferred embodiments, those skilled in the art will readily appreciate that various changes and/or modifications can be made to the invention without departing from the spirit or scope of the invention as defined by the appended claims.

What is claimed is:

1. A chromatographic system comprising:
   a) a first solvent tank containing a first solvent;
   b) a second solvent tank containing a second solvent;
   c) a first pump for drawing the first solvent from the first solvent tank and conditioning the first solvent to have a desired flow velocity;
   d) a second pump for drawing the second solvent from the second solvent tank and conditioning the second solvent to have a desired flow velocity; and
   e) a mixer assembly including:
      i. a housing having opposed upstream and downstream end portions, the upstream end portion including a fluid receiving section, the downstream end portion including a fluid discharge section having a fluid outlet formed therein, the mixer housing defining a central bore which extends axially between the fluid receiving section and fluid discharge section;
      ii. an inlet fitting engaged with the upstream end portion of the housing and having first and second fluid inlet ports formed therein that extend from the fitting exterior to the fluid receiving section of the housing; and
      iii. a mixer cartridge assembly disposed within the central bore of the housing and positioned between the inlet fitting and the downstream end portion of the housing, the mixer cartridge assembly including:
         a body portion that defines a central mixing chamber and a discharge port, the central mixing chamber communicating with the fluid receiving section of the housing and the discharge port extending from the mixing chamber to the fluid outlet formed in the housing;
         a plurality of spheres disposed within the mixing chamber for facilitating the mixing of fluids received therein; and
         a mechanism for retaining the spheres within the mixing chamber.

2. The chromatographic system as recited in claim 1, wherein in response to the first pump exhibiting flow transients, the size of the mixing chamber is selectable based on flow transient duration.

3. The chromatographic system as recited in claim 1, wherein the mechanism for retaining the spheres within the mixing chamber includes a first filter disc associated with an upstream end of the mixing chamber and a second filter disc associated with a downstream end of the mixing chamber.

4. The chromatographic system as recited in claim 1, further comprising a filter element axially disposed between the inlet fitting and the mixer cartridge assembly.

5. The chromatographic system as recited in claim 1, wherein the inlet fitting includes a male thread series that corresponds to a female thread series formed on the upstream end portion of the housing.

6. The chromatographic system as recited in claim 1, wherein the fluid inlet ports extend at an oblique angle with respect to a mixer assembly axis.

7. The chromatographic system as recited in claim 1, wherein fluid provided by the first inlet port first is contactable with fluid provided by the second inlet port in the mixing chamber.

8. The chromatographic system as recited in claim 1, further comprising a column in fluid communication with the mixer assembly.

9. The chromatographic system as recited in claim 8, further comprising a chromatographic detector operatively associated with the column.

10. A chromatographic system, comprising:
two or more solvent tanks;
a pump connected to each solvent tank and configured to draw solvent from the respective solvent tank; and
a mixer in fluid communication with the pump and having a plurality of spheres, the mixer being sized such that in response to a transient flow of solvents, the solvents are mixable by the plurality of spheres to form a blended fluid, and the blended fluid being passable through the mixer in a time period sufficient to offset the transient flow of solvent.

11. A mixer for a chromatographic system, comprising:
a housing including a central bore extending along a mixer assembly axis between an upstream fluid receiving section and a downstream fluid discharge section;
an inlet fitting engageable with the upstream fluid receiving section of the housing;
a mixer cartridge receivable in the central bore of the housing and positionable between the inlet fitting and the downstream fluid discharge section of the housing, the mixer cartridge including a mixing chamber; and
a plurality of spheres disposed in the mixing chamber for blending the two or more solvents, and
wherein a size of the mixing chamber is selectable such that two or more solvents are blendable in the mixer cartridge and passable through the downstream fluid discharge section in a predetermined time.

12. The mixer of claim 11, further comprising a first filter disc disposed at an upstream end of the mixing chamber, and a second filter disc disposed at a downstream end of the mixing chamber, for retaining the plurality of spheres.

13. The mixer of claim 11, wherein in response to a first solvent flowing into the mixing chamber by a first fluid inlet port, and a second solvent flowing into the mixing chamber by a second fluid inlet port, the plurality of spheres being configured to collide and uniformly blend the two or more solvents.

14. The mixer of claim 11, further comprising a prefilter ring positionable in the central bore of the housing and adjacent the inlet fitting, such that the two or more solvents are flowable through the prefilter ring prior to entering the mixing chamber for particulate filtering.

15. The mixer of claim 11, wherein the inlet fitting includes a first fluid inlet port and a second fluid inlet port, each extending at an oblique angle with respect to the mixer assembly axis;
wherein a first solvent is flowable from the first fluid inlet port into the mixing chamber, and a second solvent is flowable from the second fluid inlet port into the mixing chamber, such that the first and second solvents collide in the mixing chamber.

16. The mixer of claim 15, wherein the first solvent and the second solvent are suppliable to the mixing chamber by a respective first pump and a second pump.

17. The mixer of claim 16, wherein the first and second pumps are configured to supply a volume of the first and second solvents such that a free volume of the mixing chamber is a function of the size of the mixing chamber.

18. The mixer of claim 17, wherein the size of the mixing chamber is selectable to minimize a dead volume of the chromatographic system.

\* \* \* \* \*